US012620486B2

(12) United States Patent
Anthony et al.

(10) Patent No.: US 12,620,486 B2
(45) Date of Patent: May 5, 2026

(54) SYSTEM AND METHOD FOR HIGH PERFORMANCE, VENDOR-AGNOSTIC INFERENCE APPLIANCE

(71) Applicant: Analytical AI Inc., Birmingham, AL (US)

(72) Inventors: Thomas Anthony, Birmingham, AL (US); Frank M. Skidmore, Mountain Brook, AL (US)

(73) Assignee: Analytical AI Inc., Birmingham, AL (US)

( * ) Notice: Subject to any disclaimer, the term of this patent is extended or adjusted under 35 U.S.C. 154(b) by 65 days.

(21) Appl. No.: 18/087,754

(22) Filed: Dec. 22, 2022

(65) Prior Publication Data

US 2023/0238138 A1     Jul. 27, 2023

Related U.S. Application Data

(60) Provisional application No. 63/293,018, filed on Dec. 22, 2021.

(51) Int. Cl.
*G16H 50/20*          (2018.01)
*G16H 30/20*          (2018.01)

(52) U.S. Cl.
CPC ............. *G16H 50/20* (2018.01); *G16H 30/20* (2018.01)

(58) Field of Classification Search
CPC ................................ G16H 50/20; G16H 30/20
See application file for complete search history.

(56) References Cited

U.S. PATENT DOCUMENTS 9,094,580 B2 *  7/2015  Song ........................ H04N 7/18
11,640,706 B2 *  5/2023  Perticone ................. G06N 3/08
                                                                382/103

(Continued)

FOREIGN PATENT DOCUMENTS

WO          2013/033413 A1     3/2013

OTHER PUBLICATIONS

Flitton, Elsevier, 2015, pp. 2489-2499.*

(Continued)

*Primary Examiner* — Michael I Ezewoko
(74) *Attorney, Agent, or Firm* — Procopio, Cory, Hargreaves & Savitch LLP

(57) ABSTRACT

Urgent screening in high-throughput, secure environments such as emergency rooms, or security, typically involves multiple devices. Devices that are used for screening are diverse, and typically sourced from multiple vendors. Currently, devices are typically stand-alone. Further, large devices, are costly, having high capital expenses with long commercial lifetimes, sometimes approaching a decade or more. The result of these features leads to duplication of computational resources, obsolescent computational infrastructure, and lack of interconnection between elements. Aspects of this invention include a device, system, and methods to provide vendor-agnostic interconnection between the multiple elements of a defined environment. The disclosed approach untethers AI algorithms from data generation system and increases flexibility in deployment of newer technologies and algorithms. Example systems can be updated or replaced with new hardware, as computational capabilities develop on short or emergent quality improvement cycles, and can adapt nimbly to changes in threats, regulatory requirements or market developments.

19 Claims, 7 Drawing Sheets

(56) References Cited

U.S. PATENT DOCUMENTS

| | | | |
|---|---|---|---|
| 11,846,746 B2 | 12/2023 | Kair et al. | |
| 2011/0223929 A1 | 9/2011 | Boudreau et al. | |
| 2012/0229631 A1* | 9/2012 | Song | G08B 13/19663 |
| | | | 348/143 |
| 2019/0060602 A1 | 2/2019 | Tran et al. | |
| 2020/0027210 A1* | 1/2020 | Haemel | G06T 7/10 |
| 2021/0056677 A1* | 2/2021 | Perticone | G06N 3/08 |

OTHER PUBLICATIONS

Nguyen, Elsevier, 2020, pp. 1-38.*
Lu, Springer, 2020, pp. 425-438.*
Angah, Elsevier, 2020, pp. 1-9.*
Jiang, Elsevier, 2021, pp. 22-71.*

International Search Report and Written Opinion received in corresponding International Application No. PCT/US2022/053893, mailed Mar. 30, 2023, in 15 pages.
"IEEE Standard for Adoption of OpenFog, Reference Architecture for Fog Computing ; IEEE Std 1934-2018", IEEE Standard, IEEE, Piscataway, NJ USA, Jul. 31, 2018 (Jul. 31, 2018), pp. 1-176, XP068127707, DOI: 10.1109/IEEESTD.2018.8423800, ISBN: 978-1-5044-5017-1, [retrieved on Jul. 31, 2018], p. 58-p. 64, p. 85-p. 88, p. 91-p. 199.
International Preliminary Report on Patentability received in corresponding International App. No. PCT/US2022/053893, mailed Jul. 4, 2024, in 8 pages.
Substantive Examination Report received in co-pending United Arab Emirates Application No. P2024-01631, dated Dec. 30, 2025, in 9 pages, with translation.

* cited by examiner

SYSTEM AND METHOD FOR HIGH PERFORMANCE, VENDOR-AGNOSTIC INFERENCE APPLIANCE

CROSS-REFERENCE TO RELATED APPLICATIONS

The present application claims the benefit of 35 USC § 119(a) to U.S. Patent Application No. 63/293,018, filed Dec. 22, 2021, the contents of which is incorporated herein in its entirety for all purposes.

BACKGROUND

1. Field

Aspects of the example implementations are directed to systems and methods for image data processing, and more specifically, to electric digital data processing associated with a high performance, vendor-agnostic inference appliance that cannot be accessed by onsite users and/or associated devices during operation.

2. Related Art

Urgent screening in high-throughput, secure environments such as emergency rooms or security, involve multiple devices in the related art. Examples of related art devices that are used for screening are diverse, and are sourced from multiple vendors. In airport screening environments, for example, the screening of personal items, such as carried bags or (in an airport screening environment) air cargo, occurs simultaneously with on-person screening, using disparate technologies and devices. In some related art circumstances, multiple vendors with multiple screening software and device parameters may be positioned side by side in parallel screening lines.

Related art screening devices are stand-alone. Further, large devices, such as cargo and checkpoint X-ray and CT scanners, or medical CT and MRI scanners, are costly, having high capital expenses with long commercial lifetimes, sometimes approaching a decade or more. As a result, there are related art problems and disadvantages, including but not limited to duplication of computational resources, obsolescent computational infrastructure, and lack of interconnection between elements. Operationally, another disadvantage is slower screening, reduced detection efficiency, increased labor requirements, fragility (e.g., dysfunction of a single element can interrupt service), and lack of flexibility to re-organize in the context of a new disease, security threat, or new technology (e.g., artificial intelligence).

SUMMARY

Aspects of the example implementations disclosed here are directed to a device, system, process, and method to provide vendor-agnostic interconnection between the multiple elements of a defined security or medical environment, including (but not limited to) an airport screening checkpoint line, a hospital imaging center, perimeter security, or passive and active screening technology or technologies for loss prevention, without permitting the user or operator to access an appliance.

The present aspects untether (i.e., make inaccessible to onsite users and/or onsite operators during operation) artificial intelligence (AI) algorithms from data generation, and increase flexibility in deployment of additional (e.g., newer)

technologies and algorithms, without requiring the re-certification of the OEM equipment itself, which is a slow and expensive process. Some example implementations are described herein that integrate and mediate the output of multiple different vendor software packages, to present a unified dataset and image format that can be used for analysis by humans and/or algorithms.

The example implementations can be updated rapidly with new software to address new priorities or threats, adapt to new equipment, and integrate new data and algorithms as requirements develop. Example devices can be updated or replaced with new hardware, as computational capabilities develop on short or emergent quality improvement cycles. The appliance and algorithms on the appliance can be re-certified for highly regulated environments such as security and medical applications more rapidly than the entire certified system going through the recertification process. The appliance, and algorithms on the appliance, can rapidly address changes in threats, regulatory requirements, as well as market concerns and conditions.

According to these aspects, a method and apparatus is provided for accessing data from multiple devices in a vendor-agnostic fashion, and presenting data in a unified format for at least the purposes of security, loss prevention, or medical screening.

Additionally, a network-capable device capable of managing data flows is provided at actionable, relevant speeds for the environment in question, with capability for embedded software, including artificial intelligence software.

Further, a GPU based high performance and high throughput appliance is provided for AI inferencing with failover.

DETAILED DESCRIPTION

Figure 1:
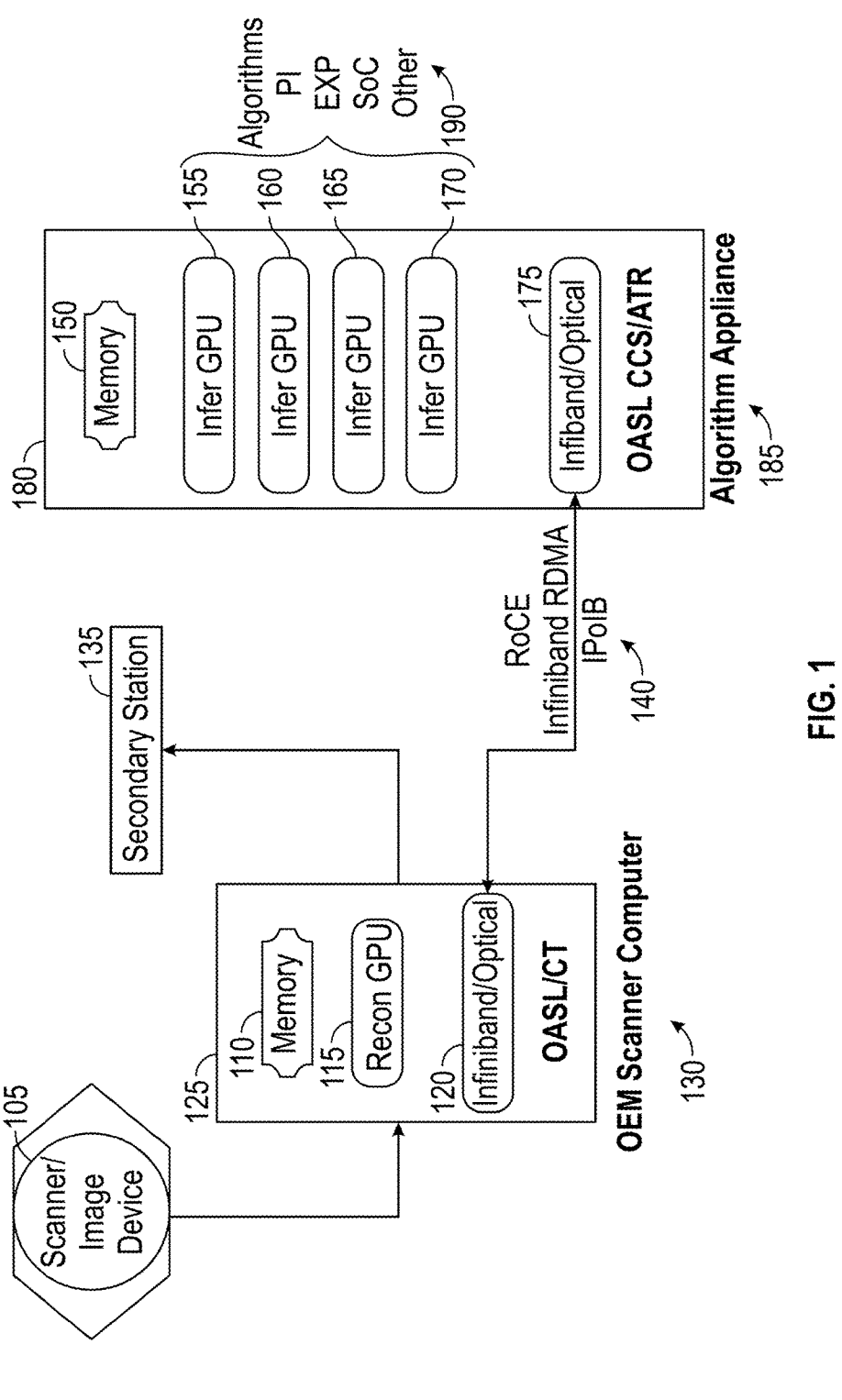
FIG. 1 illustrates a high-performance device according to the example implementations, which can interface with one or more OEM scanner computers and transfer the scanned and reconstructed images over a low latency high speed network such as InfiniBand (IB) with Remote Direct Memory Access (RDMA) to perform the automated threat recognition (ATR) inferencing with multiple algorithms over multiple GPUS.

The following detailed description provides further details of the figures and example implementations of the present application. Reference numerals and descriptions of redundant elements between figures are omitted for clarity. Terms used throughout the description are provided as examples and are not intended to be limiting. For example, the use of the term "automatic" may involve fully automatic or semi-automatic implementations involving user or operator control over certain aspects of the implementation, depending on the desired implementation of one of ordinary skill in the art practicing implementations of the present application. Further, sequential terminology, such as "first", "second", "third", etc., may be used in the description and claims simply for labeling purposes and should not be limited to referring to described actions or items occurring in the described sequence. Actions or items may be ordered into a different sequence or may be performed in parallel or dynamically, without departing from the scope of the present application.

Introduction

Aspects of the example implementations include a device, system, and methods to provide vendor-agnostic interconnection between the multiple elements of a defined security or medical environment, including (but not limited to) an airport screening checkpoint line, a hospital imaging center, perimeter security, or passive and active screening technology or technologies for loss prevention. The example implementations untether the AI algorithms from the data generation system, increases flexibility in deployment of newer technologies and algorithms, and reduces regulatory burdens or commercial overhead and expenses that would otherwise be required as computing technology, customer priorities, and algorithm sophistication develop. The example implementations are directed to a scalable, centralized platform for a Multi-Input/Multi-Output Artificial Intelligence-based algorithm hosted either on physical hardware, or in a cloud setting. A number of novel features are expected to occur through these example implementations, including but not exclusive of the following attributes:

Decoupling an algorithm from the device of an Original Equipment Manufacturer (OEM) Scanner (e.g., baggage, on-person, cargo). For example, but not by way of limitation, the algorithm may include an automated threat recognition (ATR) algorithm in the case of transportation screening security, or a medical diagnostic algorithm in the case of medical diagnosis.

A device and process supports and is supported by client-sponsored software libraries.

A device and process that can accommodate multiple threat recognition algorithms, diagnostic algorithms, or loss prevention algorithms, such as prohibited items algorithms, stroke detection algorithm algorithms, explosive detection algorithms, or other similar AI based algorithms, from different vendors and developers, on a single platform.

Load balance and failover capability incorporated in a single system, providing both security and robustness.

Algorithm changes and hardware changes (including, but not limited to, new OEM devices, or internal computational infrastructure such as Graphic Processing Unit (GPU) or Central Processing Unit (CPU) components) that can be interchanged without affecting certified equipment provided by an original equipment manufacturer (OEM).

Support for optional monitoring and remote viewing.

Proximity of a dedicated computational platform with controlled (e.g., completely restricted) access to the cloud and Internet is expected to provide resilient service, resistant to internet service attacks such as denial of service (DoS) or other challenges that occur in computational services offered in the cloud or over wireless internet. Additional advantages of a controlled access platform include but are not limited to reduced exposure of data, including private or protected data, to external actors; improved security of software systems and processes; and reduced access of network to external hacking or cyber-attack.

On-site localization of a dedicated computational platform improves resilience of the platform to power outages and other challenges in dedicated settings where accessory power is available.

Provisions are made to use high-speed communication connections with hardware elements, substantially reducing latency and improving efficiency.

Reduced latency allows for certain types of computation to occur in near real time, allowing "look back" and "look forward" features.

Regarding the present disclosure, it is noted that "identifying the location of a person, object, or item in near-real time" is defined as identifying a current, or previous location of the person, object, or item within milliseconds, seconds, or minutes of the actual time during which the person, object, or item was physically present at the location in question.

Further, "look back" is defined as a capacity to track a person, object or item in time and space to a period of time, and a location, prior to the time of alarm. In some cases, "look back" capabilities can register a person, object, or item in one camera view, and identify the person, object, or item in a second camera view at a different time.

Additionally, "look forward" is defined as a capacity to track a person, object or item in time and space to a period of time, and a location, subsequent to the time of alarm. In some cases, "look forward" capabilities can register a person, object, or item in one camera view, and identify the person, object, or item in a second camera view at a different time.

The foregoing novel features, as well as additional novel features disclosed in this application, result in inventive features ideally suited for low risk tolerance settings, such as "always on" security settings where systems must be resilient to attempted hacking, interruption of service, or power fluctuations.

Additional features that may or may not be present in various iterations are described below as example implementations.

Example Implementations

A hardware-based or cloud-based platform is provided that includes a computer server or servers having two or more GPUs and a high-speed network connection to one or more screening devices. The screening devices include but are not limited to magnetic resonance imaging (MRI) devices, X-Ray devices, Computed Tomography (CT) screeners, millimeter wave scanners, terahertz screeners, infrared imagers, metal detection devices, or ultrasound technology. Additional methods of obtaining an image may occur to individuals skilled in the state of the art. Further, while the example implementations refer to imaging, other forms of data may be processed, including but not limited to digital audio files that can be transformed into an image.

Various example implementations host multiple algorithms from multiple vendors.

Compliance with multiple imaging standards includes, but is not limited to, the Digital Imaging in Communication in Security (DICOS) and Digital Imaging in Communication in Medicine (DICOM) standards.

A network connection that uses the highest speed pathway available is disclosed. Examples of include high speed ethernet, so called "InfiniBand technology", or optical fiber technology. Interconnect pathways may evolve in the future. Accordingly, continued technology advancement beyond the representative technology noted is expected, and is incorporated as extensions of the general concept "highest speed pathway available."

When available, connections and algorithm throughput are managed using available open software platforms. An example platform that may be used in some reductions to practice include the U.S. government sponsored Open Platform Software Library (OPSL), which is an example of an open architecture software library (OASL). Multiple similar government-sponsored or commercial software platforms and libraries can be supported by this invention and may occur to individuals skilled in the state of the art.

Computation supports recognition of a desired target or condition, to improve decision triage. Example targets or conditions might include a medical condition or diagnosis, identification of a security threat, or identification of a non-permitted object or condition. An example of a medical condition or diagnosis might include the presence of a stroke, tumor, cyst, abscess, fracture, disease, or other condition that can be suspected or diagnosed based on imaging criteria in which human medical decision making may need to occur either acutely, or chronically, to prevent progression or unwanted further developments pertaining to the health of an individual receiving an imaging procedure.

An example of non-permitted objects or conditions might include objects that should have been divested (such as in an airport security environment). Another example of a non-permitted object or condition might include an object that should not be present (such as merchandise in a loss prevention utilization, or concealed data storage devices in a commercial setting such as a data center where private or proprietary information is stored).

Another example of a non-permitted item or condition might include a non-permitted individual or animal in a secure area (e.g., an animal close to a commercial or military aircraft runway, or a non-permitted individual in a secure governmental or commercial facility). Another example of a non-permitted item or condition might include deposition of a foreign body on an aircraft runway (runway foreign object debris or FOD). Another example of a non-permitted object or condition might include an individual in the vicinity of a sensitive area representing a security threat (such as an individual with a weapon or suspected explosive device detected outside of a school, office, or other location).

Multiple other examples will occur to individuals skilled in the state of the art. A purpose of the invention is not simply to store information from a detection, but rather to integrate this information into larger systems alerting humans to potential conditions, threats, or circumstances, allowing human intervention to alter, mitigate, or control the circumstances.

Facilitation of human or AI interaction to alter, mitigate, or control identified circumstances shall be known hereafter as "triage".

In some example implementations, additional automated steps may occur that facilitate human triage. In this circumstance, an operator or human agent need only interact or make triage decisions after an automated AI triage, directed by the algorithms supported by the invention. Embedded AI algorithms in this case support human decision making as to the nature of medical care, additional security steps, or other actions needed to address the alert provided by the example implementations.

FIG. 1 shows a representative hardware embodiment in the form of a device, such as a server. The device in FIG. 1 is a high-performance device that can interface with one or more OEM scanner computers 130, and transfer the scanned and reconstructed images over a low latency, high speed network using the highest speed pathway available. In this embodiment, an InfiniBand (IB) with Remote Direct Memory Access (RDMA) to perform the ATR inferencing with multiple algorithms over multiple GPUS is displayed.

Turning to FIG. 1, the figure shows a system with the following example elements. A representative OEM Scanning Device 105 is coupled to a representative OEM Scanner Computer 130 that includes memory/storage 110 to store information from the scanning device, a GPU for image reconstruction 115, and output capabilities using the "highest speed pathway available" (here represented as InfiniBand or Optical output capabilities) 120.

In this representative embodiment, the scanning device generates images from a Computed Tomography (CT) scanner in a format, including but limited to a format compliant with an open architecture software library (example—the OPSL 125).

More specifically, with respect to 125, OPSL is one representative embodiment of an OASL. However, the system, methods, and devices disclosed support software suites from any source, including open-source platforms and proprietary, privileged, or classified software platforms.

Further, a representation of the disclosed hardware includes an Algorithm Appliance 185. The Algorithm Appliance 185 includes input capabilities commensurate with the OEM Scanner Computer output capabilities (here represented as an InfiniBand or Optical input 175, memory 150 configured to receive information, and at least one inferencing GPU (in the present example, four inferencing GPUs are displayed—155, 160, 165, 170).

Pertaining to memory 150 on the Algorithm Appliance, immediate access memory to allow for management of usual processes can be combined with Archival Memory to allow for data acquisition for continual improvement of algorithms in a development environment.

Pertaining to the RoCE InfiniBand RDMA 140, linking elements 120 and 175 (e.g., InfiniBand or optical input elements), in many applications a high-speed network switch will aid in the system scaling for multiplexing for a large local networks of imaging devices or multiple such networks. RoCE InfiniBand RDMA 140 is a high-speed system. However, as technology advances occur, various interconnection methodologies may be expected depending on use case, available technology, and state of the art.

In this representative embodiment, an automated threat recognition software (e.g., a non-transitory computer-readable medium configured to execute machine-readable instructions) associated with ATR may also be compliant with the OASL 180. A series of software packages are loaded and embedded, including but not limited to software dedicated to detection of Prohibited Items (PI), Explosives (EXP), Stream of Commerce items such as laptops, shoes, or other items (SoC), or other software packages appropriate for the specific use case 190.

Pertaining to Algorithms on the Algorithm Appliance 190, in many applications Secure, Encrypted Software validation will be embedded in processes to ensure that the algorithms that are hosted are only the ones that have been approved to operate on the appliance. as an alternative to approval, vetting or certification may be performed, depending on the application.

The platform represented in FIG. 1 has a number of advantages. Some advantages of this architecture may include:

Using this platform, computation of item recognition and triage decisions can occur, and an operator/human agent could interact and conduct human triage after the automated triage has occurred.

While the specific represented embodiment focuses on a particular use case, broad use cases may be provided, such as using this platform, in some embodiments, for classification of an object, item, or circumstance to enrich and improve the efficiency of the human triage. For example but not by way of limitation, one example of classification improving triage might include a use case on an airport runway identifying the name and location of an animal (e.g. "turkey, bear"), that might represent a threat to an aircraft taking off or landing.

Another example of such a classification, in a loss prevention application, might include recognition of a non-permitted item (e.g. "suspected data storage device detected", or "suspected weapon [knife] detected"). Still another example of such a classification in transit hub might include recognition of a non-permitted circumstance (e.g. "abandoned luggage detected, please investigate").

A further example of such a classification pertaining to a medical application might include the name and localization of a medical condition (e.g. "suspected pneumothorax detected in left lower quadrant", or "suspected fracture located in right femur").

In such cases and similar circumstances disclosed above, rapid localization of the region of concern can be displayed to the human operator to allow rapid triage. More rapid triage can allow more efficient and safer management of the condition, threat, or circumstance. Various iterations and expansions of the above may be evident to those skilled in the state of the art.

As the example implementations obtain information from multiple devices, in some iterations, a comprehensive report may detail multiple areas of concern. Some example report formats might include the following elements:

"In patient [NAME] a left pelvic fracture was detected on abdominal X-ray at time [TIME], rib fractures were detected on a chest X-Ray at time [TIME], and an intracerebral hemorrhage was detected on a head CT occurring at [TIME]"; or "In quadrant [a1], GPS coordinate [x1, y1], a suspected Turkey was detected at [TIME]. In quadrant [a2], GPS coordinate [x1,y1], at time [TIME], suspected FOD was detected near runway [z]").

In various examples, localization may use more than one imaging device, and more than one detection algorithm, across multiple hardware and algorithm developers. Various additional examples may be evident will occur to those skilled in the state of the art.

In various iterations, private or public software libraries may be accessed. For example, in some security applications an open architecture library such as OPSL may be utilized to aggregate security algorithms and data streams, or for AI training. Other similar open software platforms, or proprietary software platforms exist and may be useful in other applications. A variety of arrangements therefore for shared platform, algorithm, and OEM device interaction will occur to those skilled in the state of the art.

Multiple attributes of the example system presented in FIG. 1 are provided.

First, evaluation of screening on the example system can utilize a tiered (or hierarchical) approach. Lower-level classifications can occur rapidly and be fed to actors quickly, while higher level evaluations (such as those requiring further evaluations) can occur subsequently.

Second, in centralizing and integrating computational hardware for automated screening, a single system can perform an automated artificial intelligence process such as, but not limited to recognition, localization, and/or classification, for multiplexed scanner systems.

One associated anticipated outcome of the foregoing aspect of the process might include reducing software loading and unloading times.

An additional associated anticipated outcome of this process might include enabling group level alerts of important or concerning circumstances. An example group notification might include:

"A potential explosive detection has been detected in security lane 5."

Yet another associated anticipated outcome of this process might include the ability to achieve higher level synthesis of detections. Some example notifications might include:

"Aggregate disassembled parts noted on lanes 1, 3, and 4 could be used to assemble a firearm" or "Inert components detected in lanes 1 and 2 could produce an explosive when combined"

A further associated advantage occurring through hardware centralization and integration is the enablement of common output platforms, such as a common threat recognition platform displaying results from multiple types of OEM devices.

Still an additional associated advantage occurring through hardware centralization and integration is the enablement efficient and rapid remote triage.

associated advantages beyond representative examples shown above will occur to those skilled in the state of the art.

Third, the presence of high-speed network connections allows the computer server to access scanner data at speeds nearing the speed of memory access in a fully integrated standalone screening system.

Additional associated advantages beyond representative examples shown above will occur to those skilled in the state of the art.

Figure 2:
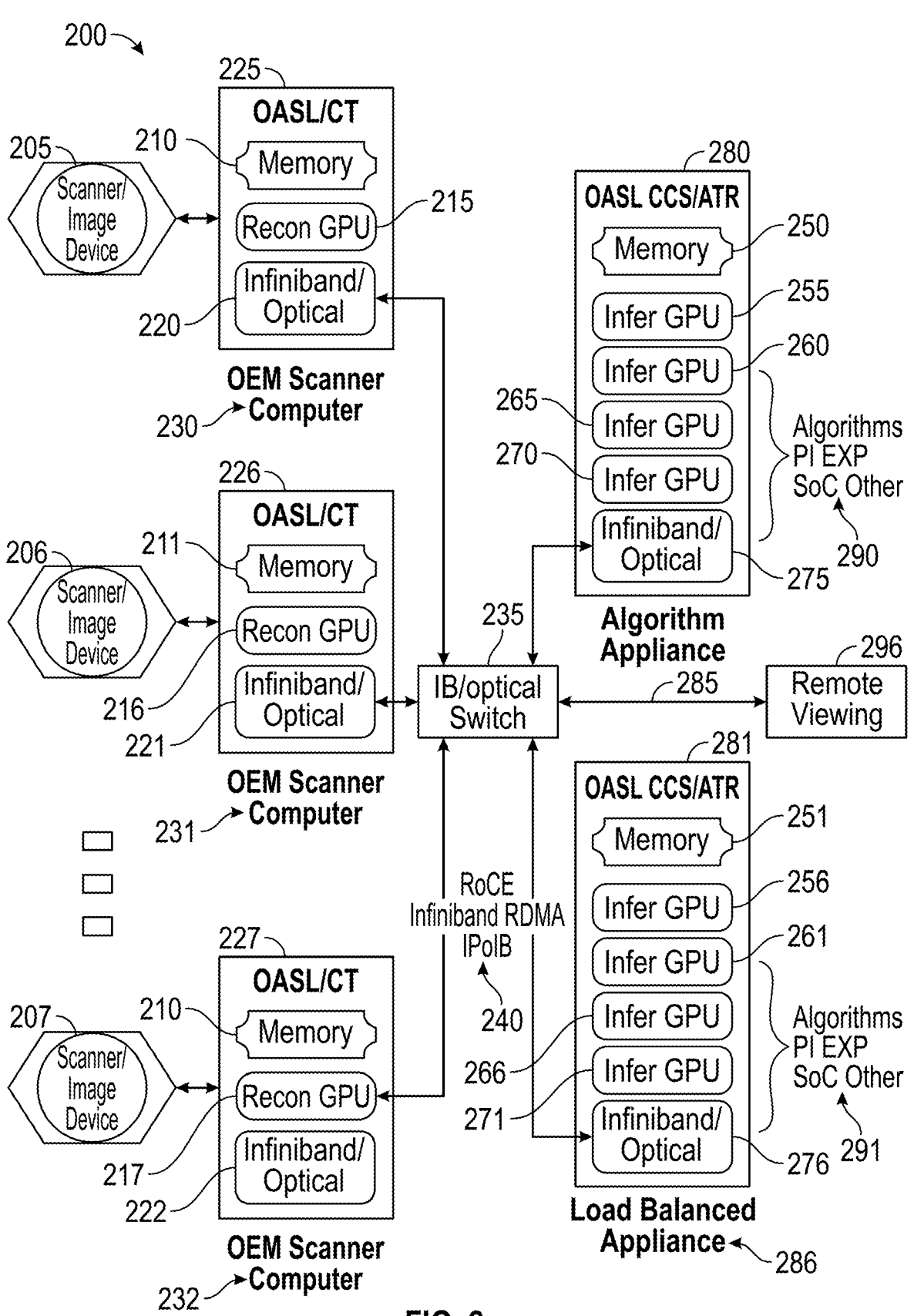
FIG. 2 illustrates a distributed system according to the example implementations, with a command and control system (CCS) located as a dedicated server. A cloud-based CCS could also be used (not shown in FIG. 2).

For scaled up systems, multiple servers can be linked together as shown in FIG. 2. Turning to FIG. 2, it can be noted in some implementations, multiple algorithms can be hosted across multiple servers. FIG. 2 represents an example of linkage of multiple sensors.

Multiple scanner devices may be linked in a network. Three scanner devices in FIG. 2 are represented as 230, 231, 232, but another number of additional scanner devices and computers can be linked. Each of the scanner computing devices 230/231/232 associated with a scanner-imaging device 205/206/207 include a memory 210/211/212, a recon GPU 215/216/217 and an optical input/output (e.g., I/O switch) 220/221/222. In various iterations, an OASL such as Open Platform Software Library (OPSL) 225/226/227 may be utilized to aggregate security algorithms and data streams, or for AI training.

A Command and Control System (CCS) can direct data to the appropriate algorithm regardless of location, using in addition an InfiniBand (TB) or Optical Switch 235, or other interconnection methodology suited to the specific use case. Further, the Optical Switch 235 may be coupled to remote viewing at 296.

Linkage of multiple scanners to a single Algorithm Appliance via switch 235 is represented as 285, with a second Load Balanced Algorithm Appliance 286 available for circumstances in which data flow is at a peak, or a malfunction or problem with the first Algorithm Appliance 285. Each of the appliances 285/286 includes a memory 250/251, one or more inference GPUs 255-270/256-271, an optical input/output (e.g., I/O switch) 275/276. In various iterations, an OASL such as Open Platform Software Library (OPSL) 280/281 may be utilized to aggregate security algorithms and data streams, or for AI training.

One purpose of load balancing, in this case, is to improve resilience and reliability of the system in the face of potential system failures. Specifically, it can be noted that in this representation, the processes integrated with the CCS will maintain appropriate load balancing across interconnected systems. For example, in this circumstance if a single GPU, server, or platform is unavailable or slow due to the number of processes already running, the distributed system will re-allocate that data to an idle server process available in the distributed network.

Another purpose of load balancing is to allow for scheduled maintenance, system updates, or other activities to occur seamlessly without altering system capabilities.

An aspect of the example implementations includes treating AI algorithm capacity as a needed "critical infrastructure". "Critical infrastructure" is often over-engineered. Buildings, and bridges are engineered not simply to manage a load, but also to manage unexpected challenges, and be resilient to degradation. In a similar fashion, systems, methods, and processes are presented to generate a secure, resilient system for delivering AI in critical security, safety, loss prevention, medical, and other applications.

Turning again to FIG. 1 and FIG. 2, it can be noted that in some iterations, multiple algorithms are hosted on a single machine (for example, refer to 190, 290, 291). The capability to host and manage multiple algorithms provides an advantage in that algorithms can be managed by a variety of secure systems. As technology and algorithm management advances, additional systems with this sort of capability will continue to develop and will occur in the future to those skilled in the state of the art.

Figure 3:
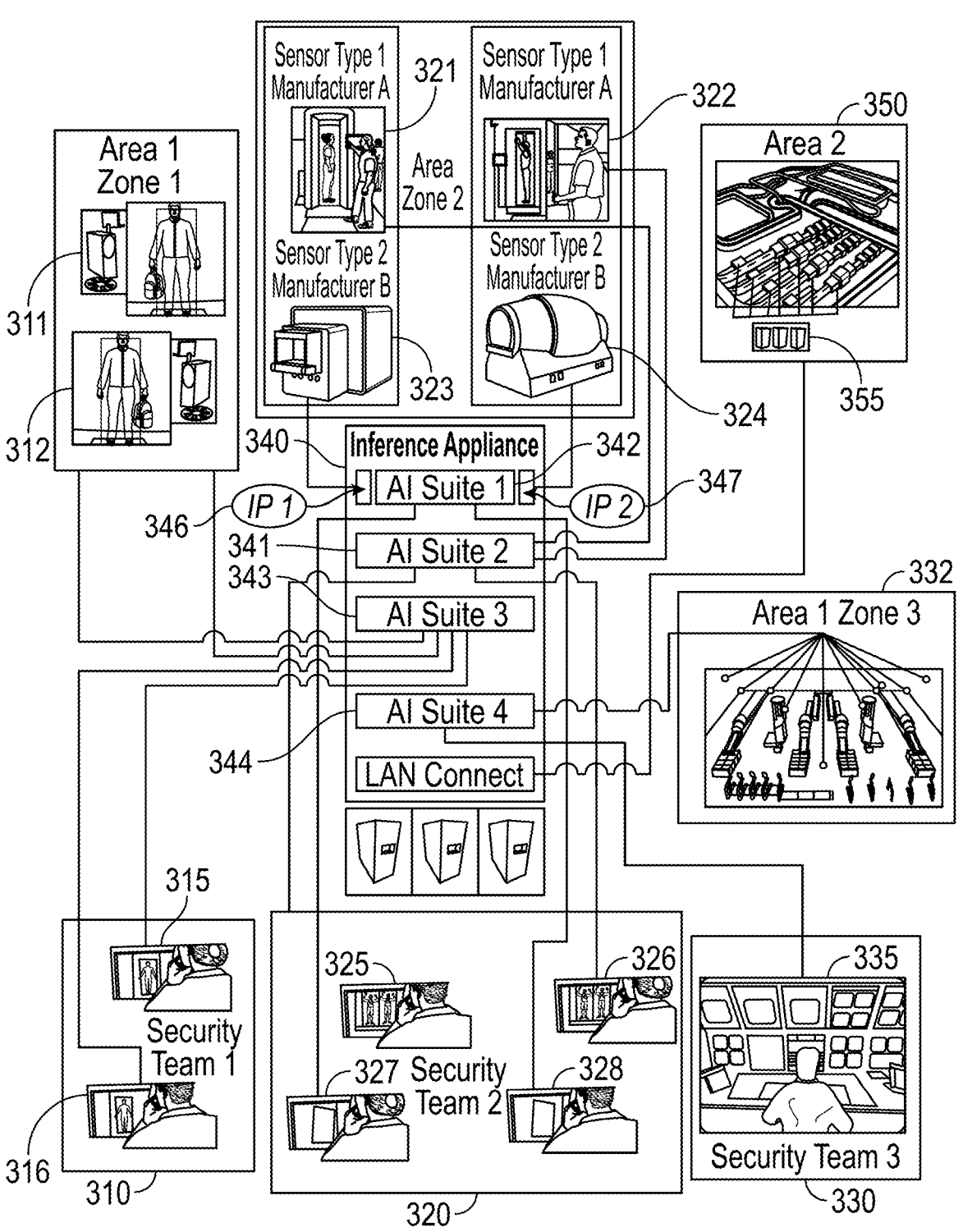
FIG. 3 illustrates an example implementation of a secure system in a complex security environment.

FIGS. 1 and 2 have shown a practical implementation of the device. An example practical implementation from a user-facing perspective is shown in FIG. 3. Turning to FIG. 3, a representative embodiment involving airport security is shown as this sort of example is familiar to many in the general public.

In this example implementation, an appliance device, labelled Inference Appliance 340, is represented. The appliance device utilizes one or more computational units 341, 342, 343 for computation and load balancing (3 are shown in this example). The appliance device 340 interacts through high-speed connections (gray lines of varying weights) to three security zones (Zone 1, Zone 2, Zone 3). An organizational schematic shows the relationship between computational algorithms and devices.

Summarizing FIG. 3, the appliance supporting security tasks are shown in specific security zones 310, 320, 330, and 340. While specific sensors in current use for security are displayed as examples, many types of sensors used in secure, high-trust environments can be assumed to have similar characteristics. Additional arrangements of sensors and different types of sensor networks will occur to those skilled in the state of the art. In the representative embodiment shown in FIG. 3:

A Security Team 1 at 310, involving one or more agents (2 are displayed as 315, 316) is associated with a checkpoint utilizing one or more passive terahertz-wave imaging in Area 1, Zone 1 (two shown, sensor devices labeled 311, 312). The sensors 311 and 312 have AI solutions computed by AI Suite 3 343. AI Suite 3 343 includes a series of integrated machine learning, artificial intelligence, and image processing software systems optimized to generate solutions from passive terahertz images (see FIGS. 1, 2, 4, 5, and 6 for details).

A Security Team 2 (320) is associated with a checkpoint utilizing one or more active millimeter-wave scanners (two shown, labeled 321 and 322) and one or more computed tomography (CT) scanners (two are shown, labeled 323 and 324).

Millimeter-wave scanners in this context are used for screening of individuals in a divested setting for prohibited items. Some individuals in Security Team 2 are focused on evaluating results from millimeter-wave screening (two individuals shown, labeled 325 and 326). AI solutions from millimeter-wave screening have AI solutions computed by AI suite 2 341, comprised of a series of software programs with characteristics similar to AI Suite 3 343, optimized for millimeter-wave detection parameters.

CT scanners in this context are used for screening of luggage. Some individuals in Security Team 2 are focused on evaluating results from CT luggage screening (two individuals shown, labeled 327 and 328). AI solutions from CT screening have AI solutions computed by AI suite 1 labeled 342. In this case, however, CT scanner 323 is a device manufactured by manufacturer B, and CT scanner 324 is a device manufactured by manufacturer C. In this case, distinct image processing software and logic (IP1 and IP2, labeled 346 and 347) may be required to allow appropriate analysis by AI Suite 1. In other cases, the two manufacturers may require entirely distinct AI Suites optimized to individual specific devices.

A Security Team 3 (330), is associated with soft target monitoring in pre-check (and as appropriate post-check) areas by monitoring a large number of video feeds. A "soft target" in this context may include any individual or target object that is in an area where un-vetted or unscreened individuals, processes, devices, or systems are present.

Turning to Security Team 3, a series of sensors provide data through high-speed connections to the Inference Appliance 340. AI solutions are computed by AI Suite 4 (344). At least one unique feature characterizes the requirements of Security Team 3, including the following aspect.

Unlike security agents 315, 316, 325, 326, 327, and 328, a single human agent in Security Team 3 (one shown, 335) may monitor a large number of screens at once. This is a common circumstance in the case of building security, perimeter security, and other similar settings where large geographic regions are being monitored.

In this case, a rapid scene-analysis AI protocol may be used. Many such algorithms are available; one recent example of a type of algorithm used for this purposes is the algorithmic approach referred to as "You Only Look Once" (YOLO).

Agents in Security Team 3, rather than attending to one screen, are alerted to a screen and location when a potential concerning circumstance is detected (represented in this case by black arrow, pointing to screen labeled 351).

Area 2, labeled 350 demonstrates a second security zone. In the context of this demonstration, Area 2 represents a checked baggage area. In Area 2, a separate Inference Appliance, labeled 355, has distinct algorithms dedicated to distinct sensor characteristics and requirements. The representation demonstrates that a communication between two separate Inference Appliances may in some cases be used to improve or optimize overall system performance and efficiency.

Summarizing FIG. 3, specific sensor types and relationships are shown to provide a relevant example of the complexity of sensor types and relationships in security, medical technology, and loss prevention. The example is meant to touch on some of the complexities of these types of networks, and support the example implementations referenced in this patent and associated claims. Some representative points elucidated by this use case include, but are not limited to:

Algorithm design, specifications, and purpose are task-specific. This disclosure supports multiple tasks on one platform.

Organizing distinct, task-specific algorithms on one platform allows for the efficient development of communication between algorithms, and between humans involved in collaborative tasks.

Summarizing the above points two points, FIG. 3 demonstrates that AI support can be optimized as a human-centered activity. Decision support is designed to improve human decision making among members of a team with different roles.

The disclosed example implementation (interchangeably called the Inference Appliance or Algorithm Appliance), allows for more robust and informed interactions between various team members.

Elucidating this point, consider a circumstance where a weapon is discovered by agent 327, monitoring CT data. The present embodiment allows immediate notification of agent 325, and agent 335, that an individual in screening, or who had recently existed screening, had a weapon detected in a carry-on bag.

In summary, FIG. 3 displays a secure platform hosting multiple vendor-agnostic AI algorithm suites, optimized to function in a holistic fashion across a complex environment with multiple distinct security protocols and purposes. Detailing some advantages of this system:

One or more secure appliance system(s) can monitor multiple sensors, easing the burden on human agents.

Vendor-agnostic algorithms allow consistent and reliable performance across the security checkpoint.

Threat information can be transmitted to agents within a specified area, or rapidly across multiple areas.

Communication latency is optimized to allow optimal decision time and, when appropriate, robust "look forward" and "look back" capabilities to identify past and current position of alarmed persons or objects.

The system demonstrates resilience and robust performance during interruptions in internet service or power interruptions.

The system has limited to zero external access. Results of this limitation in external access includes:

Reduced exposure of data, including private or protected data, to external actors.

Improved security of software systems and processes.

Reduced access of network to external hacking or cyber-attack.

Hardware and software updates are not tied to equipment lifetimes, and rapid updates to either hardware or software are supported.

Figure 4:
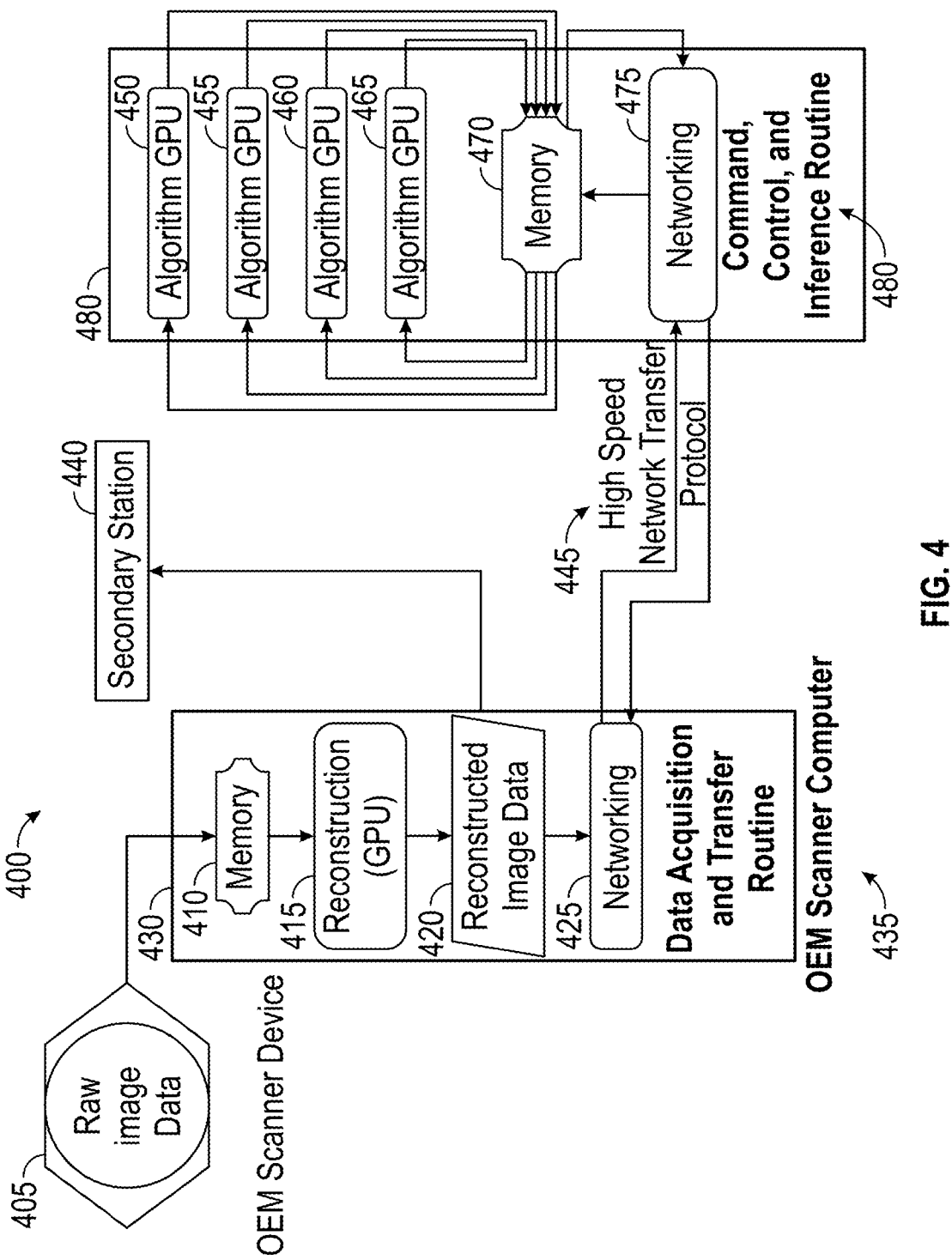
FIG. 4 shows a simplified example of a logic-flow through the disclosed systems and devices, according to the example implementations.
Figure 5:
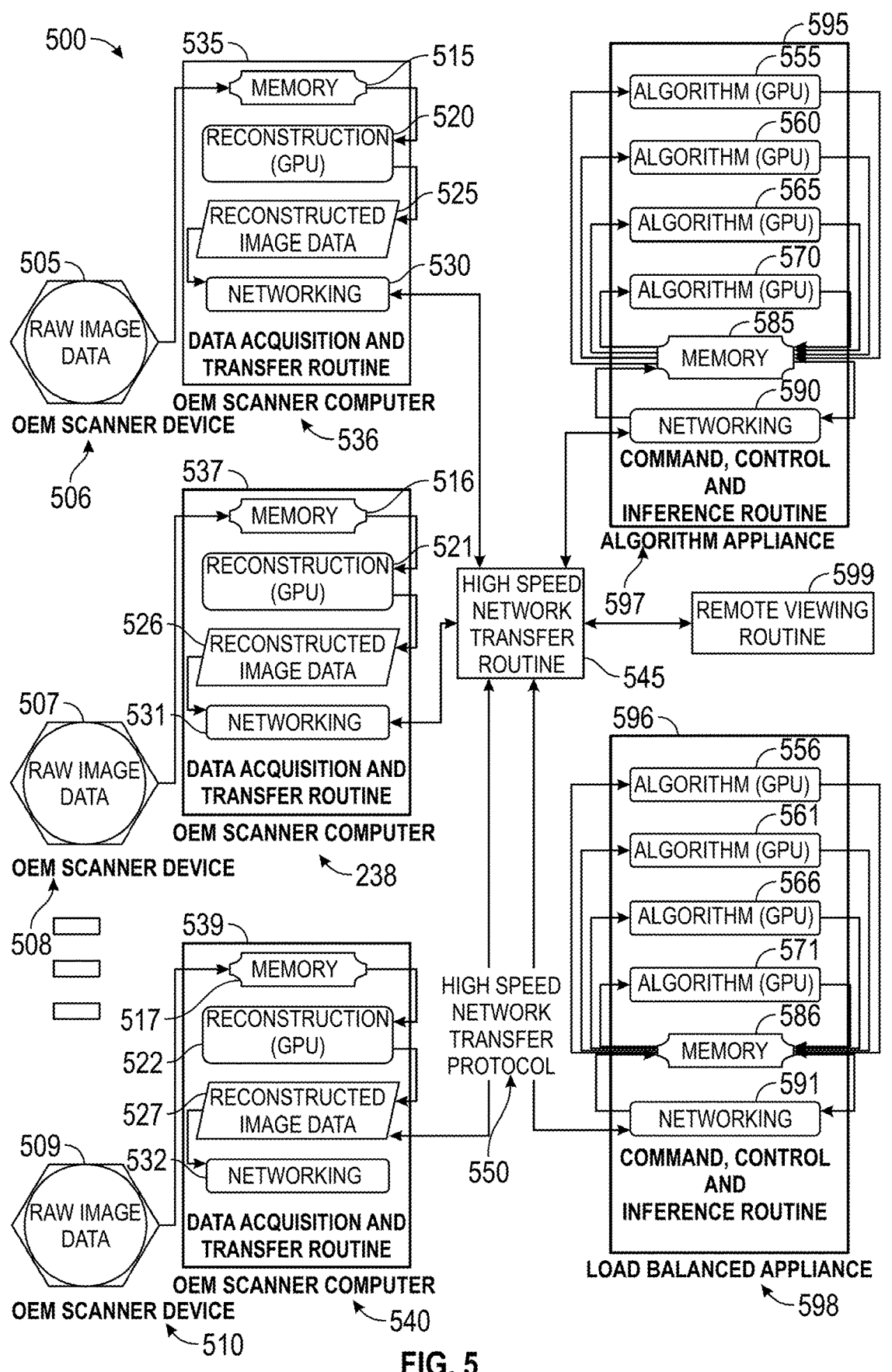
FIG. 5 shows an example of a logic-flow through the disclosed systems with multiple input devices and load balancing/failover capabilities, according to the example implementations.

In FIG. 3, the human-facing aspects of the disclosed devices, systems, and methods are described. In order to provide the novel, human-centered features of the device, the aspects of FIG. 4 and FIG. 5 are provided. Specifically, a relevant feature of the disclosed device(s) pertains to management of data in an environment where multiple vendors use vendor-specific software packages to transform sensor information into images.

A representative simplified example of a typical logic-flow from an original equipment manufacturer (OEM) to the disclosed appliance device is represented in FIG. 4. Summarizing FIG. 4, raw information from a sensor or series of sensors is collected at 406 by a scanner device, transitions to an OEM computational platform 435, and is connected via a high-speed connection 445 to an algorithm appliance device 485. The elements of the foregoing devices are the same as described above with respect to FIG. 1.

A representative logic flow through the OEM device starts with Raw Image Data 405 transitioning to a data Acquisition and Transfer Routine 430 involving hardware and software located on an OEM Scanner Computer 435. A representative logic flow through the OEM Scanner Computer would include:

Transfer of Raw Image Data from sensors 405 transitioning to internal memory 410.

Generation of an image from raw image data from raw data in memory, such as using a GPU 415, resulting in Reconstructed Image Data 420.

Transition of the image to the disclosed device, here labelled the Algorithm Appliance 485, through a high speed connection, using High Speed Network Transfer Protocols 445, via switch 425.

A correlated logic flow then occurs on the Algorithm Appliance, using a Command, Control, and Inference Routine 480. The Command, Control, and Inference Routine displayed in FIG. 4 as 480 is a representative example of an AI suite shown in FIG. 3 (see FIG. 3, AI Suite 1, AI Suite 2, AI Suite 3, and AI Suite 4). Detailing further the Command, Control, and Inference Routine 480] a series of steps can be detailed.

First, reconstructed image data must reside in memory 470 accessible to AI algorithms.

Second, a AI algorithms, running on various graphics processing units (GPUs) access the data from memory (see 450, 455, 460, 465). Algorithms represented as 450, 455, 460, 465 may independently assess data, or data may pass between algorithms.

Data from algorithmic analysis returns to memory (470), and is passed back to a networking card (475).

Subsequently, the resulting assessment can either be forwarded directly to a secondary station, such as a viewing station 440 for merging with image data or returned back to the OEM device via a High-Speed Network Transfer Protocol 435 to the OEM Scanner Computer for merging. In FIG. 4, the second process is represented.

FIG. 4 shows the following data flow:

Raw data 405 transits through an OEM Scanner Computer 435 using a Data Acquisition and Transfer Routine 430 to generate reconstructed image data 420.

Reconstructed data 420 transits via a High-Speed Network Transfer Protocol 445 to a Command, Control and Inference Routine 480 located on an Algorithm Appliance Device [480].

Inferencing occurs on one or more GPUs, using AI Algorithms 450, 455, 460, 465, operating singly or collaboratively to generate a threat representation.

A return of inferencing to the OEM Scanner Computer 435 occurs using a High speed Network Transfer Protocol 445.

Forwarding of a modified or merged image from the OEM computer to another device, such as a viewing station 440. The modified or merged information includes both data from the OEM device, and additional, AI-generated, inferencing information from the Algorithm Appliance.

While FIG. 4 represents one, specific methodology, modifications of this logic flow may occur, depending on the nature of the OEM device, the specific data characteristics, and desired efficiencies for high-speed data flows.

Comparing FIG. 4 to FIG. 3, a logic flow is provided in FIG. 4 that in FIG. 3 is represented as a logic flow from various OEM devices (located in FIG. 3, Zone 1, Zone 2, and Zone 3) to an OEM appliance (FIG. 3, Inference Appliance), with merged data eventually arriving at various users or Security Teams (Security Teams 1, 2 and 3) in the form of a useful image with AI assisted localization of an circumstance of concern or object of interest (or absence of such).

FIG. 5 shows a distributed logic flow, involving a series of OEM devices. The elements of the foregoing devices are the same as described above with respect to FIG. 2. In FIG. 5, the following is represented:

Raw images (505, 507, 509) being generated from various OEM Scanners (506, 508, 510).

Reconstructed Images (525, 526, 527) being generated through a variety of vendor-specific Data Acquisition and Transfer Routines (535, 537, 539), with each vendor specific routine located on a vendor-specific OEM scanner computer (536, 538, 540).

Transiting of data through a High Speed Network Transfer Routine 545 to one or more Algorithm Appliance Computational Platforms (597, 598).

AI Inferencing occurring through various GPU-based AI algorithms (555, 560, 565, 570, 556, 561, 566, 571).

Return of Inferencing Information through a High Speed Network Transfer Routine 545 to distribute information back to the OEM devices (536, 538, 540) and to one or more Remote Viewing Routines 599.

The remote viewing routine then distributes relevant information to viewing stations. In the context of the example shown in FIG. 3, the remote viewing routine sends this information to the various security teams.

In FIG. 4 and FIG. 5, logic flow through hardware elements are displayed.

Figure 6:
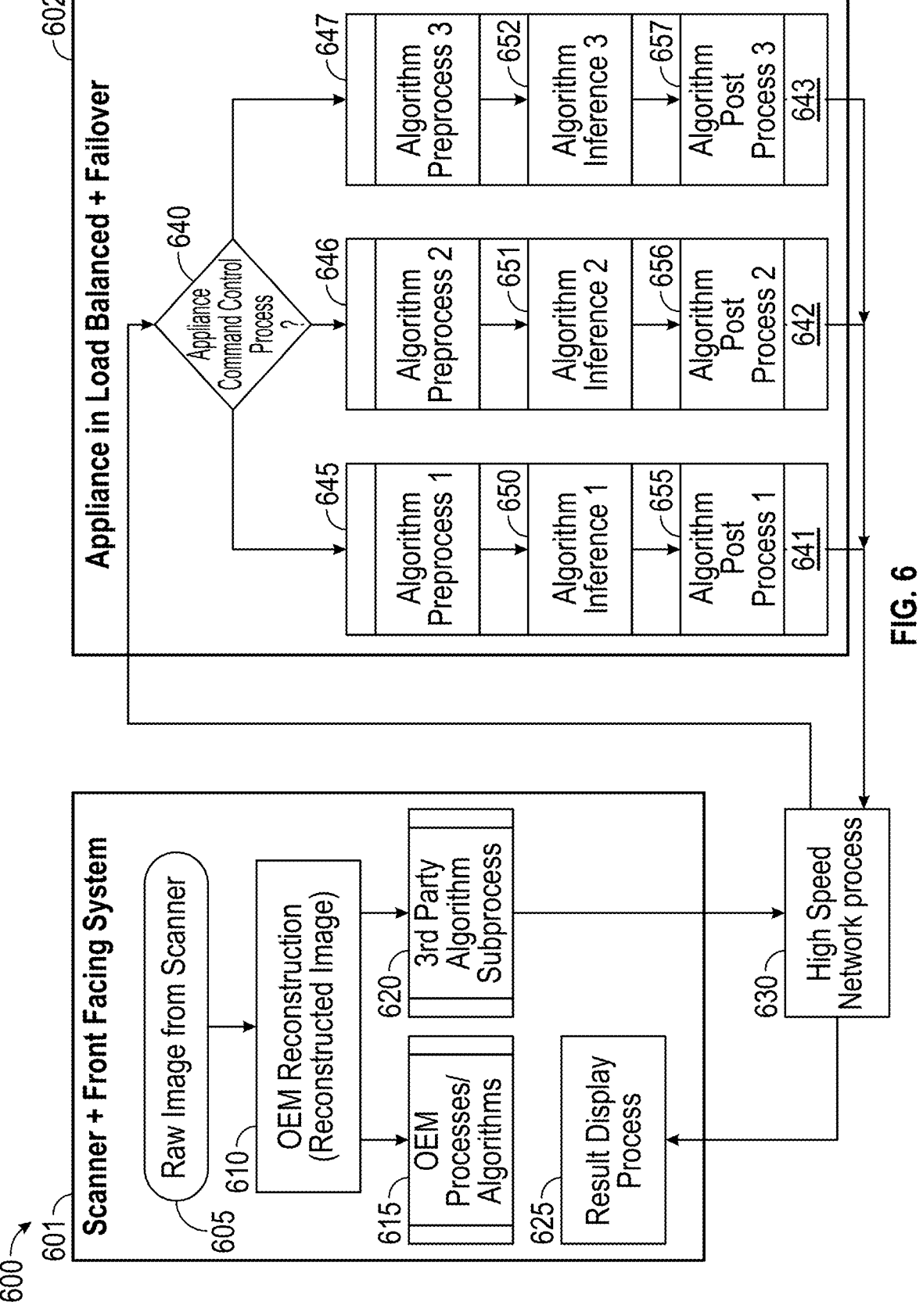
FIG. 6 shows a representative management of data and analyses in an algorithmic process flow diagram, according to the example implementations.

In FIG. 6, a schematic is now presented showing one representative example of a software organization and associated data flow and processing across the elements disclosed earlier. Turning to FIG. 6, software, systems, and methods can be divided into a Scanner and Front Facing System (601) and an Algorithm Appliance/Load Balancing and Failover System (602), with interconnections (620, 625, 630, 640).

The Scanner and Front Facing System 601 represents the external elements that link to the Appliance Systems, Processes and Methods.

The Appliance/Load Balancing and Failover System 602 in this context serves as a schematic diagram incorporating the systems, methods, processes, and devices disclosed in this patent. Interconnections (not shown) are provided between outward facing systems and the disclosed systems, methods, processes, and devices (620, 625, 630, and 640).

Turning to a representation of outward-facing systems 601, it can be noted that raw data is generated from an imaging scanner 605, and a Reconstructed Image is generated. In some cases, the reconstructed image is generated by a proprietary OEM Reconstruction Software (610) as displayed in FIG. 6. In other cases, a third party may be responsible for image reconstruction and Reconstruction Software.

The Reconstructed Image 610 in this representation then transitions to usual OEM processes and algorithms (615).

In the context of the systems, methods, processes, and devices disclosed, the Reconstructed Image in this representation is also forwarded to a third-party algorithm subprocess 620. The third-party Algorithm Subprocess represent a connection point between the disclosed systems, processes, methods, and devices and the OEM device.

The third-party algorithm in this representation is subsequently forwarded to a High Speed Network Process 630, which forward data to an Appliance Command and Control Process 640.

Once data has been transferred to the Appliance Command and Control Process 640, systems and methods previously disclosed allow various OEM images to be appropriately distributed to various algorithm suites, such as one or more of those shown in FIG. 3. In this context:

Algorithm preprocess 1 (645), Algorithm Inference 1 (650), and Algorithm post process 1 (655) is analogous to AI Suite 1 in FIG. 3.

Algorithm preprocess 2 (646), Algorithm Inference 2 (651), and Algorithm post process 2 (656) is analogous to AI Suite 2 in FIG. 3.

Algorithm preprocess 3 (647), Algorithm Inference 3 (652), and Algorithm post process 3 (657) is analogous to AI Suite 3 in FIG. 3.

Alternatively, several algorithms could operate as part of a single or series of analyses on a specific OEM image (i.e., 641, 642, 643) could all be included in a single software suite, integrating in various ways with a single OEM image.

Subsequent to post processing, in the represented example algorithm results are integrated with appropriate OEM Reconstructed Image 610 through a third-party algorithm 620, via a High-Speed Network Process 630, and forwarded to an outward facing Results Display Process 625 supporting one or more functions, including providing AI-augmented information to a team involved in a high-trust environment devoted to human or system safety, security, or health.

Turning specifically to the Algorithm Appliance 602, a more detailed description of the process starts with discussion of the purpose of the command and control process. Once the image data is received by the appliance, the Command-and-Control process 640 determines the appropriate algorithm and GPU the data needs to be routed for inference and subsequent post-processing. Subsequent processes follow.

Process 641/642/643/660 shows macro processes inside the appliance. Depending on the number of compute devices (GPUs) available on the appliance these processes can be run in parallel on the same image or different images depending on the use case.

Processes 641/642/643 are schematic representations of computational processes (three representations shown) subserving a primary function of the Algorithm Appliance in providing coordinated AI output to users. While three processes are shown, an arbitrary number of processes are expected to be handled by a given Algorithm Appliance depending on task requirements and hardware capabilities. Pertaining to Processes 641/642/643, The reconstructed image is sent to the appropriate preprocess step 645/646/647 to get the image in a format compatible and processed for the model to work on.

This preprocess step could include multiple subprocesses. Examples of some preprocess methodologies including scaling the image to the correct shape/size for the AI model to inference on, adding noise (salt and pepper), changing image color, representing the image in grayscale, ray tracing etc.

All preprocess steps may have functions that could be understood by those skilled in the state of the art.

In some cases, preprocess steps are "data augmentation" steps. Here, "data augmentation" is a step dedicated to increasing the robustness or stability of an AI model.

For example, adding salt and pepper noise, changing image scale, changing color parameters, thresholding images, image distortion, reflection, or rotation, and similar steps that will occur to individuals skilled in the art can expand presented data, allowing for the generation of a more robust solution resilient to real world environments.

In other cases, some preprocess steps, in addition or supplementing a data augmentation purpose, can assist in localization of an object, or defining object borders. Ray tracing and thresholding are examples of preprocessing steps that can both assist in data augmentation by allowing multiple views of a potential target to be presented and provide more precise localization within an image of a desired target.

In summary, preprocessing data within the algorithm appliance serves the important purpose of improving the robustness of third-party algorithm AI solutions in real world environments.

The preprocessed data is then sent to the AI inference process 650/651/652. AI Inference is achieved through an "inference engine" that applies logical rules to the knowledge base to evaluate and analyze preprocessed data and provide an actionable result. These processes can be standard AI inference algorithms (e.g. resnet, yolo) or custom algorithms built for particular problems (detecting threats in CT scans in bags, or on persons at airports, detecting strokes in the brain in CT images, etc.)

The output of the AI inference process provides a result that in some cases may need a post process step 655/656/657. Postprocessing of third-party AI algorithms may also be applied. For example:

Postprocessing may be needed to allow the results to re-integrate with the original OEM image to allow presentation to an outside use.

Postprocessing may be needed to allow results from one manufacturers device to be presented on another manufacturers platform.

For example, global alerts across multiple systems require a step to allow the data to be presented to multiple display devices.

Further, development of certified, comparable datasets at different sites enables the development of novel external facing processes.

For example, consider the example shown in FIG. 3 and discussed earlier. In this example, it could be the case that a particular site, such as a particular airport, may have a greater than expected number of false positives detections.

In this representative example, the existence of certified results across multiple sites enables the development of external record keeping applications reporting detections, compared to non-detections.

Such an enabled application could allow third-party algorithms and regulatory entities to track algorithm performance by site. Benefiting parties from such an enabled result could include.

Third-party algorithm manufacturer

Airport

Government regulatory agencies

OEM manufacturers are also considered to be users of the system. The Algorithm Appliance can store data from usual activity to provide robust data from the field. This robust data can facilitate important quality control functions. For example:

Data from a single manufacturer can be stored over time. Analysis of processes from a single manufacturer over time provides the following advantages:

Quality control over time pertaining to machine output can be stored and analyzed, allowing measurement that can detect machine degradation and rapidly detect machine malfunction.

Data can be stored that can be used for the manufacturer or third parties to obtain increasing amounts of data for improvement of algorithms or equipment.

Data from many manufacturers can be compared. The ability to compare data from multiple equipment manufacturers allows for regulatory agencies to compare and contrast output quality across domains of detectors.

In the related art, the proprietary nature, and siloed availability of OEM data often prevents such comparisons.

The current disclosure therefore may allow for regulatory agencies to significantly improve quality across entire fields or domains of operation, using the features and capabilities described herein.

Regulatory agencies and the hosting entities (such as airports, other transport hubs, hospitals, schools, or entities using the appliance for loss prevention or perimeter security) are also considered uses of the Algorithm Appliance. Data on the Algorithm Appliance, when allowed and applicable, can be provided to these entities for quality metrics and team development.

With respect to the above, more broadly, a potential perimeter security breach at a nuclear plant could be rapidly transmitted to a number of locations both locally and remotely through secure transmission protocols.

Further, and also with respect to the above, the presence of a medical emergency such as a stroke could be transferred securely to multiple users in a medical application.

In some cases, user notifications may serve an immediate function. Again turning to the example discussed in FIG. 3, in a security environment individuals monitoring security cameras may rapidly notify other agents in a secure fashion (through the results display process) of an impending concern. Similarly, individuals at a particular screening location may be able to rapidly notify individuals monitoring cameras that an individual or group of individuals requires monitoring and tracking.

Multiple additional examples will occur to individuals skilled in the art.

Allowing multiple AI algorithms to function in a coordinated fashion across a diverse environment involving multiple human teams, multiple manufacturers, and in multiple settings in a reliable, robust, and resilient fashion, with user facing functions is a key novel feature of the represented systems, processes, methods, and devices. The diversity of user-facing functions afforded by the Algorithm Appliance for human agents, commercial and government organizational users, equipment manufacturers, and regulatory agencies is an additional key novel feature of the represented systems, processes, methods, and devices.

The systems, processes, methods and devices disclosed can be applied to many environments. FIG. 3 illustrates a specific security application (an airport security environment), but similar complex environments are present in a variety of settings, including for conditions or circumstances that require regional collaboration to provide optimal service or care. Such applications include, but are not limited to:

Integrated Customs and Border Protection devices to provide intelligent, integrated information across multiple border checkpoints.

Port-of-entry AI networks for detecting cargo container anomalies.

Integrated loss prevention networks for places of business, or data centers.

Devices at the locations involved in regional care networks, including (but not limited to) stroke, cardiovascular disease, or trauma care networks where feeder or lower acuity hospitals have partnered with higher level care centers for interventional care.

Devices at large hospital ERs where rapid diagnostic capabilities across multiple devices would be beneficial to triage care.

Transportation settings such as commercial rail environments or metropolitan transit environments (buses, metro, rail).

Large commercial warehouses and "wish fulfillment" centers.

Critical power infrastructure settings, from power grid substations to power plants (including nuclear power plants).

Military bases or civilian security stations such as police stations.

Multiplexed security systems involving multiple sensor types and locations, such as secure perimeters in which optical information, terahertz or infrared, radar, or other data-streams are combined to provide complex information across multiple equipment types and algorithms.

Figure 7:
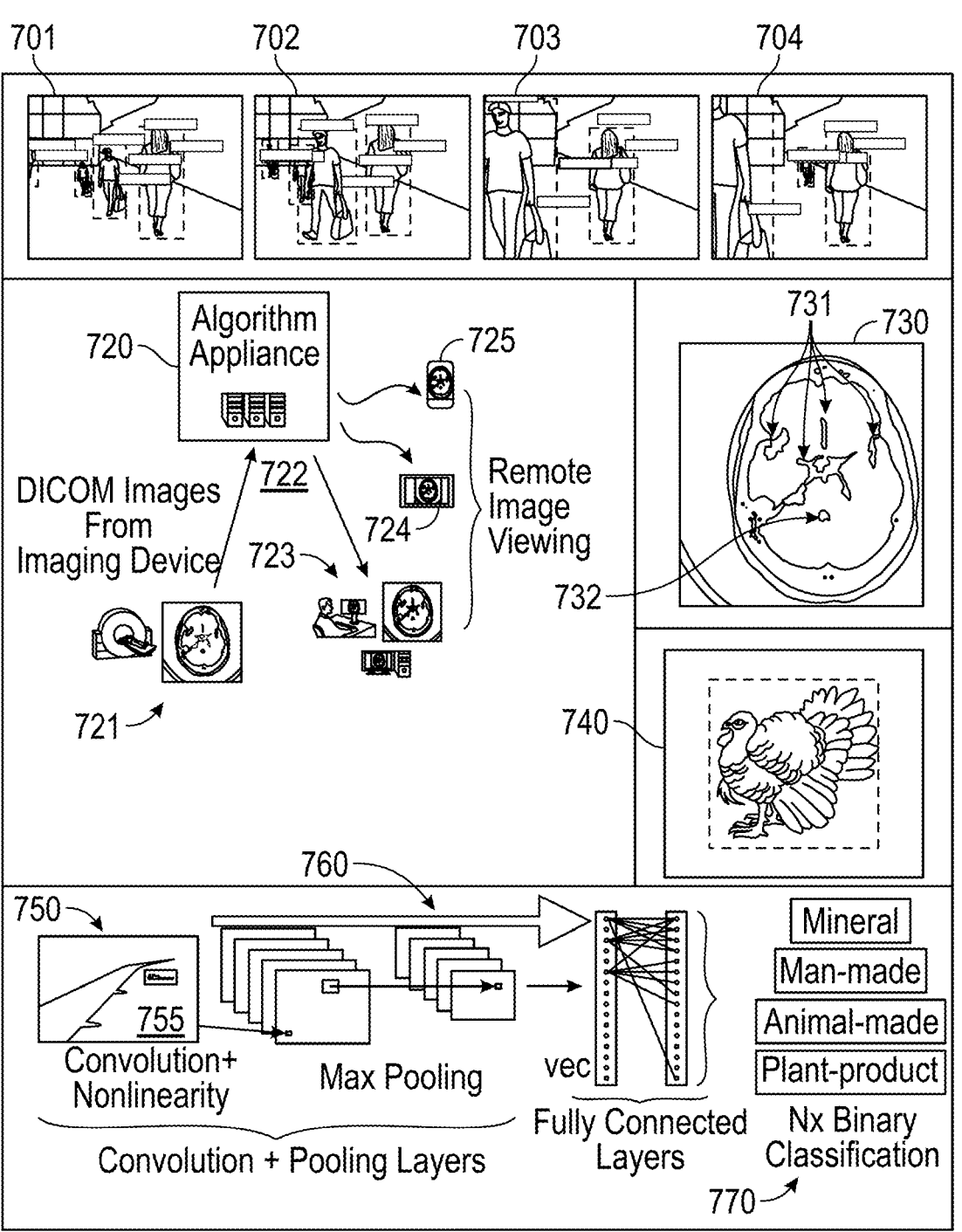
FIG. 7 illustrates multiple representative example representative embodiments in which the disclosed systems, processes, methods, and devices can improve system and human performance and function, according to the example implementations.

FIG. 7 shows a few examples of various AI software implementations. These images are a limited demonstration that these applications are not speculative, but rather represent critical emergent technology applications in need of the novel solution described in this disclosure. Specifically, FIG. 7, items 701, 702, 703, and 704 show sequential frames from a low-definition camera. The items show output from an AI algorithm suite applied to pair luggage with associated individuals and identify abandoned luggage. The specific approach in question uses an AI approach referred to as "You Only Look Once" (YOLO), but multiple similar algorithms have been developed that can track items in near-real time on sequential images. Using the processes, methods, and devices disclosed in this patent, a number of unique and novel enhancements are available, such as the following enhanced features Input from multiple individual sensors (in this case optical cameras) are combined, allowing individuals to be tracked from one camera to another seamlessly in near-real time.

Identification of potential concerns or security threats can be integrated with other information, such as information gathered from other sensor systems.

Integration with other network systems can provide enhanced near-real time look-forward and look-back capabilities across distributed camera systems and through other system sensor systems.

System-wide alerts can be distributed across a secure local area network.

Protected or confidential information, including sensitive security systems, information, and methods, are protected with the local area network.

Load balancing and fail-over capabilities, along with capability to transmit to remote sensors, result in a robust system, resilient to point attacks, communication disruptions, and power outages.

Returning to FIG. 7, items 701, 702, 703, and 704, it should be noted that while the AI algorithm suite demonstrated in this example is specifically focused on identifying and tracking luggage and bags, similar approaches can be used for identifying other sorts of objects, such as drones, or individuals with weapons. These features lead to applications for multiple secure systems in "always on" security environments such as transit stations, perimeter security monitoring, and other public settings such as schools, stadiums, or supermarkets.

In FIG. 7, 720 represents a secure, AI-based medical platform. In an increasingly insecure cyber environment, applications in medical settings may be focused on securely managing access and AI assessment of protected health information (PHI).

Similar to the system displayed in FIG. 3, an imaging device 721 provides information to an Algorithm Appliance 722, which then can distribute information for remote viewing including hardwired secure systems (723) as well as wireless devices (tablet device represented by 724, mobile phone represented by 725). In this case the repository of protected health information and hospital internal systems are protected within a secure local area network, with wireless output of limited information sent only to specific, verified users.

Item 730 shows an example medical application. In 730, a subarachnoid hemorrhage (731) has been detected by an AI algorithm suite in a CT scan, with an additional detection of intraventricular hemorrhage (732).

Item 740 shows an identification of a Turkey in a perimeter security system. Far from being a benign presence, some territorial wildlife can be a threat, including to both military and commercial airplanes.

In 750 shows an example of an AI algorithm detecting foreign object debris (FOD) on a runway, including a detection (755), processing through an AI algorithm (760) with object identification (770). Pertaining to 750, an AI algorithm time is disclosed.

Rather, the inventive systems, methods, devices, and processes in this disclosure recognize that in many settings, optimal use of AI requires integration of one or more AI algorithms or algorithm suites to support complex goals, such as the complex goals required to provide services dedicated to protecting human or system health, safety, or security.

When humans collaborate in a high-trust environment, only trusted, vetted members participate in the team. AI increasingly supports human teams involved in critical tasks, becoming a force-multiplier and augmenting agent for human teams. The systems, processes, devices, and methods disclosed provide secure hardware and software systems to support and mediate optimal use of trusted, verified, and secure collaborating AI algorithm support in high-trust environments.

A few, limited example implementations have been shown and described. These example implementations are provided to convey the subject matter described herein to people who are familiar with this field. It should be understood that the subject matter described herein may be implemented in various forms without being limited to the described example implementations. The subject matter described herein can be practiced without those specifically defined or described matters or with other or different elements or matters not described. It will be appreciated by those familiar with this field that changes may be made in these example implementations without departing from the subject matter described herein as defined in the appended claims and their equivalents.

What is claimed is:

1. A computer-implemented method for collecting and processing data from multiple devices to generate an actionable output for security screening or medical screening in secure environments, the method comprising:

receiving data associated with an image from at least one of the multiple devices;

providing the received data to a processor, and performing data acquisition at the processor;

transferring the data, via a high-speed network, to an appliance;

at the appliance, performing command, control and inferencing by one or more graphical processing units (GPUs) to generate the actionable output, wherein the inferencing comprises automated threat recognition (ATR) for the security screening, decoupled from a scanner that scans the image to generate the data associated with the image, wherein the appliance is not accessible by any device during operation;

using an ATR algorithm to perform a detection and at least one of a look-back analysis and a look-forward analysis to track a condition in time or space, wherein the look-forward analysis comprises registering a person, object, or item in one camera view, and identifying the person, the object, or the item in a second camera view at a different time; and providing the actionable output, via the high-speed network, for executing an action, wherein the data is accessed from the devices of multiple software and hardware vendors, in a manner that is independent of the software and hardware vendors, and further wherein multiple ATR algorithms can be executed on the appliance.

2. The computer-implemented method of claim 1, wherein the command, control and inference comprises security detection threat to identify security threats.

3. The computer-implemented method of claim 1, wherein the command, control and inference comprises applying artificial intelligence to automatically detect actionable threats without input by a user.

4. The computer-implemented method of claim 1, wherein the command, control and inference comprises identifying critical medical conditions or diagnoses.

5. The computer-implemented method of claim 1, wherein the command, control and inference comprises applying artificial intelligence to automatically detect disease or conditions without input by a user.

6. The computer-implemented method of claim 1, wherein the data from the multiple devices is presented and managed in a common format.

7. The computer-implemented method of claim 6, wherein the common format comprises at least one of a United States DICOS (Digital Imaging and Communications in Security) imaging format, a DICOM (Digital Imaging and Communications in Medicine) imaging format, or a Unified File Format (UFF).

8. The computer-implemented method of claim 1, wherein the look-back analysis comprises tracking a history of an identified object or an individual before an event common format comprises a DICOM (Digital Imaging and Communications in Medicine) imaging format.

9. A system for collecting and processing data from multiple devices to generate an actionable output, the system comprising:

a scanner device configured to scan data associated with an image from at least one of the multiple devices;

a processor configured to receive the scanned data and perform data acquisition;

a high-speed network configured to transfer the data from the processor to an appliance; and the appliance configured to perform command, control and inference by one or more graphical processing units (GPUs) to generate the actionable output, wherein the inference is associated with automated threat recognition (ATR) for a security screening, decoupled from a scanner that scans the image to generate the data associated with the image, wherein the appliance is not accessible by any device during operation, wherein the actionable output is provided, via the high-speed network, for executing an action, wherein the appliance uses an ATR algorithm to perform a detection and at least one of a look-back analysis and a look-forward analysis to track a condition in time or space, wherein the look-forward analysis comprises registering a person, object, or item in one camera view, and identifying the person, the object, or the item in a second camera view at a different time, and wherein the data is accessed from the devices of multiple software and hardware vendors, in a manner that is independent of the software and hardware vendors, and further wherein multiple ATR algorithms can be executed on the appliance.

10. The system of claim 9, wherein the appliance is configured to process the data at speeds configured for security screening, and presenting and managing data in a common format.

11. The system of claim 9, wherein the high-speed network has connect capability that is embedded.

12. The system of claim 9, wherein a graphical user interface (GUI) is located only at a remote area, only allowing remote access and monitoring of security activity.

13. The system of claim 9, wherein one of the multiple software and hardware vendors can connect to one or more other ones of the multiple devices to access a network of devices.

14. The system of claim 9, further comprising access points that are geographically remote, so as to permit allowing screening and networking capability based on geography.

15. The system of claim 9, wherein a single one of the appliance can support multiple lanes of a security checkpoint.

16. The system of claim 9, wherein the appliance is configured to reduce compute, power and cooling required at the processor while providing failover and redundancy, and to perform load balancing such that if one of the GPUs fails, another of the GPUs provide a required compute for proper operation of a security facility.

17. The system of claim 9, wherein the scanner device comprises an X-Ray or computed tomography (CT) screener for baggage, a millimeter wave screen, or a terahertz screener, and the high-speed network is high speed ethernet, InfiniBand, or optical networking.

18. The system of claim 9, wherein connections are managed through an open architecture software library.

19. The computer-implemented method of claim 1, wherein the scanner is configured to scan data associated with an image from at least one of the multiple devices without performing inference associated with the ATR for the security screening.

* * * * *